United States Patent [19]

Müller et al.

[11] Patent Number: 5,458,885
[45] Date of Patent: Oct. 17, 1995

[54] BASIC ACTIVE COMPONENT-PERMEABLE PRESSURE SENSITIVE ADHESIVE POLYMER MATERIAL PROCESS OF THE PRODUCTION THEREOF AND USE THEREOF

[75] Inventors: Walter Müller, Neuwied; Zbigniew Czech, Koblenz; Günter Simon, Hillesheim; Joerg Reinhard, Ehrenkirchen, all of Germany

[73] Assignees: LTS Lohmann Therapie-Systeme GmbH & Co., KG of Germany, Germany; Sandoz AG, Switzerland

[21] Appl. No.: 366,370

[22] Filed: Dec. 29, 1994

Related U.S. Application Data

[63] Continuation of Ser. No. 260,679, Jun. 16, 1994, abandoned, which is a continuation of Ser. No. 147,012, Nov. 3, 1993, abandoned, which is a continuation of Ser. No. 871,570, Apr. 20, 1992, abandoned, which is a continuation of Ser. No. 758,525, Sep. 6, 1991, abandoned, which is a continuation of Ser. No. 649,164, Jan. 31, 1991, abandoned, which is a continuation of Ser. No. 323,048, Mar. 10, 1989, abandoned, which is a continuation of Ser. No. 136,411, Dec. 22, 1987, abandoned.

[30] Foreign Application Priority Data

Dec. 22, 1986 [DE] Germany ............... 36 43 987.8

[51] Int. Cl.$^6$ ............................................ A61F 13/02
[52] U.S. Cl. ................................... 424/448; 524/555
[58] Field of Search ........................ 424/448; 524/555

[56] References Cited

U.S. PATENT DOCUMENTS

| | | | |
|---|---|---|---|
| 3,475,363 | 10/1969 | Garder | 526/310 |
| 3,790,533 | 2/1974 | Samour | 526/310 |
| 3,950,398 | 4/1976 | Klein | 526/310 |
| 3,981,987 | 9/1976 | Linke et al. | 526/310 |
| 3,990,459 | 11/1976 | Papantoniou | 526/310 |
| 4,246,370 | 1/1981 | Lewis et al. | 526/310 |
| 4,529,772 | 7/1985 | Druschke et al. | 526/310 |
| 4,788,267 | 11/1988 | Chiao et al. | 526/310 |

FOREIGN PATENT DOCUMENTS

| | | | |
|---|---|---|---|
| 392393 | 3/1964 | Japan | 526/310 |
| 468986 | 3/1971 | Japan | 526/310 |
| 231116 | 3/1969 | U.S.S.R. | 526/310 |
| 919038 | 2/1963 | United Kingdom | 526/310 |

OTHER PUBLICATIONS

Official Gazette 1046 TMOG–2 Aug. 1, 1984.

*Primary Examiner*—Joseph L. Schofer
*Assistant Examiner*—N. Sarofim
*Attorney, Agent, or Firm*—Kalish & Gilster

[57] ABSTRACT

A transdermal system employing a basic active component-permeable, pressure sensitive adhesive polymer material, particularly for use with basic active components for use in transdermal administration of systemically or topically acting medicaments constituted by such active components. The adhesive polymer is a homopolymer or copolymer produced using basic monomers preferably on an acrylate base. A process for production of the polymer material comprises mixing monomers suitable for the production of an adhesive by polymerization with basic monomers which can be polymerized and copolymerizing the mixture. The adhesive composition is in particular useful with basic active components in salt form and in which the therapeutically active agent is a Lewis base.

18 Claims, 1 Drawing Sheet

BASIC ACTIVE COMPONENT-PERMEABLE PRESSURE SENSITIVE ADHESIVE POLYMER MATERIAL PROCESS OF THE PRODUCTION THEREOF AND USE THEREOF

This application is a continuation of application Se. No. 08/260,679 filed Jun. 16, 1994, now abandoned, which is a continuation, of application Ser. No. 07/758,525, filed Sep. 6, 1991, now abandoned, which is a continuation, of application Ser. No. 07/649,164, filed Jan. 31, 1991, (abandoned), itself a continuation of Ser. No. 07/323,048, filed Mar. 10, 1989 (abandoned), itself a continuation of Ser. No. 07/136,411, filed Dec. 22, 1987 (abandoned).

DESCRIPTION

The invention relates to a basic active component-permeable, pressure sensitive adhesive polymer material, particularly for use with basic active components, a process for the production thereof and the use thereof.

Skin compatible pressure sensitive adhesive acrylic based polymer materials for fixation of common plasters onto the skin comprising up to 24 wt. % dimethyl aminoethyl methacrylate and other basic amin-monomers as starting material are known, e.g. from GB-PS 1,166,682 and U.S. Pat. No. 3,790,533. In the GB-PS 1,166,682 the dimethylaminoethylmethycrylate helps to adjust the viscosity of a latex while in the U.S. Pat. No. 3,790,533 the dimethyl aminoethyl methacrylate is added to free acid contained in the starting material for the polymerization in stoichiometric quantity to neutralize the same.

A particularly preferred use of the present polymer materials is in transdermal, therapeutic devices making it possible to transdermally administer systemically or topically acting medicaments.

Such transdermal devices essentially comprise a carrier film impermeable for the active component and optionally adjuvants, a pressure sensitive adhesive layer and an interposed active component reservoir. The pressure sensitive adhesive layer need not completely cover the active component reservoir and in special cases is merely constructed as an adhesive edge. Between the active component reservoir and the pressure sensitive adhesive layer or the skin, there can also be a membrane or diaphragm controlling the delivery of the active component. Such therepeutic systems are e.g. disclosed in U.S. Pat. Nos. 3,734,097, 3,598,112, 3,249,109 and 3,797,494, European patent 0 033 615 and German patents 21 35 533 and 28 22 317.

Adhesive materials used for fixing active component-containing reservoirs to a substrate to which they supply the active component at a predetermined rate are known.

In the simplest case, the pressure sensitive adhesive layer is identical with the active component reservoir. The pressure sensitive adhesive layer serves to anchor the transdermal system to the skin for the duration of the application. The adhesive active component reservoir or the adhesive layer of such a system can be protected by a peel-off protective film prior to use. The migration of the active component from the transdermal system into and through the skin takes place through passive diffusion. Thus, a good diffusion rate of the active component in the transdermal system is very important for the function thereof.

It is decisive for the function of such transdermal systems that the active component can pass through the lipophilic barrier of the human cornea. In order to achieve this, it may be necessary to use an adjuvant called a penetration accelerator.

EP-A-0155229 proposes the use of basic active component reservoirs having hydrophilic, swellable polymers, in order to speed up active component transfer through the water absorption of the polymer from the skin. However, the teaching of EP-A-0155229 of making polymers hydrophilic and swellable and thereby improving the delivery of the active components, does not always lead to satisfactory results for active component release.

Many medical active components contain one or more basic nitrogen atoms in the molecule and can therefore either be used as a free base, or as a salt of the active component base with an acid suitable for this purpose in pharmaceutical preparations. Salts have the advantage of better solubility in aqueous solvents and in many cases also that of better stability, so that salts are frequently the end point of many medicament syntheses, (important for oral administration).

However, for the transdermal administration of such systemically acting medicaments, in most cases the base, i.e. alkali which is less suitable from the storage standpoint, is superior to the salt, because as a result of its higher lipophily it can more easily penetrate the lipophilic barrier of the human cornea.

The problem of the present invention is therefore to provide a novel, pressure sensitive adhesive polymer material which, compared with the prior art devices, has an improved active component delivery for basic active components.

This problem is inventively solved in that the pressure sensitive adhesive polymer is a homopolymer or copolymer produced using basic monomers, preferably an acrylate-based polymer.

Due to the fact that use is made of an adhesive polymer having basic characteristics through polymerizing in, for example in adhesive active component reservoirs at least partly formed from the inventive composition, the active component base can be released from active component salts and can diffuse through the skin as a lipophilic base. In particularly preferred manner, the polymer is an acrylate-based copolymer.

A preferred embodiment of an inventive polymer material is obtained through the per se known polymerization of: a) between 30 and 70% by weight and preferably approximately 40 to 60% by weight of one or more alkyl esters of acrylic and/or methacrylic acid with 4 to 12 C-atoms in the alkyl radical, b) 5 to 85% by weight and preferably approximately 15 to 50% by weight of one or more amino esters of acrylic and/or methacrylic acid or other olefins which can be polymerized into a polyacrylate with basic groups, c) 0 to 50% by weight and preferably approximately 5 to 20% by weight of one or more alkyl esters of acrylic and/or methacrylic acid with 1 to 3 C-atoms in the alkyl radical, d) 0 to 15% by weight, preferably 0.5 to 12.5, more preferably 1.0 to 9 and in particularly preferred manner 5 to 8% by weight of one or more monomers which can be polymerized in with reactive groups suitable for secondary crosslinking, e) 0 to 30% by weight and preferably 2 to 15% by weight of other vinyl compounds which can be polymerized in, and f) 0 to 5% by weight and preferably 0.3% by weight of divinyl compounds which can be polymerized in, in which the sum of all the percentages in the inventive polymer material is always 100.

The invention also relates to a process for producing a composition by mixing monomers suitable for the production of an adhesive by polymerization with basic monomers which can be polymerized in and copolymerization of the mixture in per se known manner.

The invention also relates to the use of the inventive compositions for the administration of basic active components, particularly those in salt form in therapeutic systems.

The therapeutically active part of the active component salt can contain one or more basic nitrogen atoms. A preferred use of the inventive polymer material is with bopindolol and its derivatives.

The basicity and quantity of the polymerized-in basic monomers establish via the chemical equilibrium which is obtained which proportion of active component is in each case present as a free base in the system. This equilibrium is obtained if during use free active component base diffuses out of the system this equilibrium is constantly restored if, during use, free active component base diffuses out of the system, so that, assuming that there is no drop below the necessary minimum quantity of basic auxiliary groups, ultimately all the active component used as salt is transferred into the free base.

Due to the different permeation capacity of active component salt and active component base through the human skin, this leads to the new possibility of controlling the in-vivo release of the active component from the transdermal system through influencing the chemical equilibrium through varying the basicity and quantity of the polymerized-in monomers with functional basic groups.

In principle, all adhesive polymer compositions suitable for medical uses can be modified in the aforementioned manner, monomers with basic functional groups being polymerized in.

It may be necessary to incorporate into the finished adhesive material substances with influence the cohesion, tackiness, stability and/or release behavior.

DETAILED DESCRIPTION OF DRAWINGS

Figure 1:
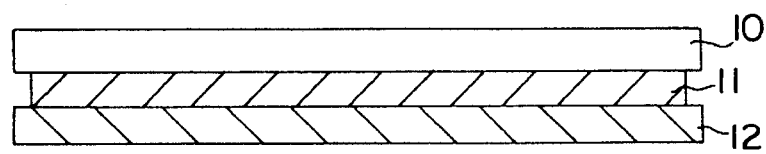
FIG. 1 is a cross-sectional view of a transdermal device of the present invention.

In FIG. 1, a carrier film 10 is applied a reservoir 11 consisting of a pressure sensitive adhesive mixed with a medically active component. The mixture comprises the medically active component reservoir. The reservoir is protected with a peel-off protective film 12.

Figure 2:
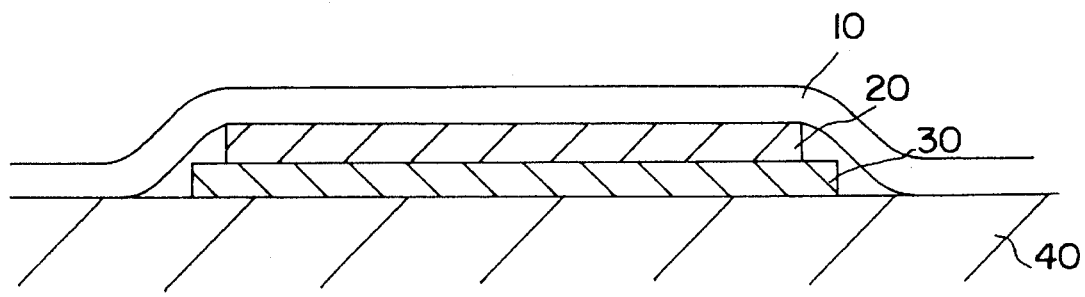
FIG. 2 is a cross-sectional view of a transdermal device of the present invention.

In FIG. 2, wherein to a carrier film 10 is applied a reservoir 20, the reservoir comprising a medically active component. The reservoir is covered with a pressure sensitive adhesive 30 through which the medically active component permeates. The transdermal device is applied, adhesive-side down to the skin 40.

DESCRIPTION OF EMBODIMENTS

The invention is explained in greater detail hereinafter on the basis of polyacrylate-based adhesives, but these examples are in no way intended to restrict the protective scope.

Acrylate-based adhesive materials are prepared by radical copolymerization of acrylic acid derivatives and other olefinic monomers in solution or dispersion. Adhesiveness-inducing acrylic acid derivatives are e.g. methyl, ethyl, n-propyl, isopropyl, n-butyl, isobutyl, t-butyl, pentyl, hexyl, heptyl, octyl, isooctyl, 2-ethylhexyl, nonyl, decyl, isodecyl, dodecyl acrylic and/or methacrylic acid esters.

As monomers with reactive groups for a subsequent secondary crosslinking, it is e.g. possible to use acrylic acid, methacrylic acid, β-carboxyethyl acrylate, crotonic acid, maleic acid, fumaric acid, itaconic acid, citraconic acid, monoesters of maleic acid with methyl, ethyl, n-propyl, isopropyl, n-butyl, isobutyl, t-butyl, hexyl, cyclohexyl, 2-ethylhexyl, octyl, isooctyl, decyl, dodecyl, isodecyl alcohol, maleic anhydride, citraconic anhydride, itaconic anhydride, maleic, fumaric and itaconic monoamide, hydroxymethyl acrylate, hydroxymethyl methacrylate, 2-hydroxyethyl acrylate, 2-hydroxyethyl methacrylate, 2-hydroxypropyl acrylate, 2-hydroxypropyl methacrylate, glycidyl acrylate, glycidyl methacrylate and allyl glycidyl ether.

Known crosslinking agents are e.g. polyisocyanates, metal chelates, metallic acid esters and melamine-formaldehyde resins.

Secondary crosslinking gives the adhesive its medical stability and cohesion.

It can sometimes be advantageous to ensure a certain crosslinking during polymerization. This is achieved through the addition of suitable divinyl compounds, which can e.g. divinyl benzene, 1,3-butadiene, divinyl adipate, diallyl adipate and vinyl acrylate.

Other monomers giving the adhesive favorable characteristics can e.g. be vinyl acetate, styrene, methyl vinyl ether, ethyl vinyl ether, n-butyl vinyl ether and vinyl pyrrolidone.

As these special adhesives are to have basic characteristics, it is necessary to use monomers with the corresponding basic groups, which can be e.g. and without claiming to constitute a complete list t-butyl aminoethyl, dimethyl aminoethyl, dimethyl aminomethyl, t-butyl aminomethyl, diethyl aminoethyl, diethyl aminomethyl, methylethyl aminoethyl, methylethyl aminomethyl acrylate or methacrylate or variously substituted aminostyrenes.

Suitable radical starters for polymerization are e.g. azoisobutyronitrile, dibenzoyl peroxide, dilauryl peroxide, t-butyl perpivalate, peroctoate and peracetate.

The polymerization solvents can in particular be acetone, methyl ethyl ketone, cyclohexanone, ethyl acetate, butyl acetate, benzene, toluene, xylenes, hexane, heptane and mixtures thereof.

The examples describe the production of active component-containing transdermal systems with different reservoir structures. In all cases bopindolol hydrogen malonate has been used as the active component, but virtually all active component groups of the different indication fields contain active components which are suitable for transdermal administration with the aforementioned structure. Reference is made in exemplified manner to antirheumatics, analgesics, blood pressure-influencing products, antiallergics, antiphlogistics, β-receptor-blockers, calcium antagonists, anti-asthmatics, dermatics, bleeding-aiding agents, geriatrics, sedatives, cardiacs, coronary agents, antimigraine agents, muscle relaxing agents, neural therapeutics, hormones and their inhibitors, antihyperkinetics and cytostatics.

The transdermal systems produced were tested on the basis of a proven method using the skin of hairless mice and rats as a model for the human skin.

EXAMPLE 1

Production of an adhesive acrylate-based composition with polymerized-in basic groups 1a) 100 g of dimethyl aminoethyl methacrylate, 93.5 g of 2-ethyl-hexyl acrylate, 6 g of acrylic acid and 0.6 g of azoisobutyronitrile as radical chain starters are dissolved in 130 g of ethyl acetate and refluxed for 3 hours. After cooling to room temperature the adhesive is ready for use. The viscosity is 2.0 Pa.sec at 22 deg.Celsius (Brookfield viscosimeter).

1b) 40 g of dimethyl aminoethyl methacrylate, 52.7 g of 2-ethyl-hexyl acrylate, 7 g of acrylic acid, 0.3 g of vinyl acrylate and 0.3 g of azoisobutyronitrile are dissolved in 70 g of ethyl acetate and refluxed for 3 hours. The adhesive is ready for use after cooling to room temperature.

1c) 130 g of dimethyl aminoethyl methacrylate, 60 g of 2-methyl-heptyl acrylate, 1.0 g of n-propyl-acrylate, 0.3 g of vinylacrylate and 0.3 g azoisobutyronitrile are dissolved in 70 g of ethyl acetate and refluxed for 3 hours. The adhesive is ready for use after cooling to room temperature.

1d) 60 g of dimethyl aminoethyl methacrylate, 130 g of n-dodecylacrylate, 10 g of n-propylacrylate and 0.3 g of azoisobutyronitrile are dissolved in 100 g of ethyl acetate and refluxed for 3 hours. The adhesive is ready for use after cooling to room temperature.

1e) 50 g of dimethyl aminoethyl methacrylate, 140 g of i-amylacrylate, 10 g of methylmethacrylate, 1 g vinylmethacrylate and 0.3 g of azoisobutyronitrile are dissolved in 150 g of methyl ethyl ketone and refluxed for 3 hours. The adhesive is ready for use after cooling to room temperature.

1f) 40 g of diethyl aminomethyl methacrylate, 80 g of n-butyl-methacrylate, 40 g of ethyl methacrylate 1 g vinyl methacrylate and 0.3 g of azoisobutyronitrile are dissolved in 100 g of ethyl acetate and refluxed for 3 hours. The adhesive is ready for use after cooling to room temperature.

1g) 120 g of diethyl aminoethyl methacrylate, 60 g of n-butyl methacrylate, 20 g ethylmethacrylate, 1 g vinyl methacrylate and 0.3 g of azoisobutyronitrile are dissolved in 100 g of ethyl acetate and refluxed for 3 hours. The adhesive is ready for use after cooling to room temperature.

EXAMPLE 2 (COMPARISON EXAMPLE)

Production of a transdermal therapeutic device 79.0 g of a 42% by weight solution of an acrylate-based adhesive (DUROTAK 280-2416 of NATIONAL STARCH CHEMICAL B.V., Netherlands), 0.9 g of triethyl citrate, 12.5 g of bopindololhydrogen malonate and 40.0 g of methyl ethyl ketone are combined accompanied by stirring and following complete and thorough mixing applied to a siliconized, aluminized, 100 µm thick polyester film. After drying for 15 minutes at 50° C., it is covered with an aluminized 15 µm thick polyester film. For a coating thickness of 100 µm, there is a weight per unit area of 32 g/m and an active component content of 8.4 g/m.

EXAMPLE 3

Production of transdermal therapeutic devices with a polymerized in-basic group-containing adhesive 3a) 52.7 g of a 60% by weight solution of acrylate adhesive in ethyl acetate, as described in example 1a), 1.6 g of a 7.5% by weight solution of titanium acetyl acetonate in isopropanol, 0.9 g of triethyl citrate and 12.5 g of bopindolol hydrogen malonate in 40 g of methyl ethyl ketone were processed in the manner described in example 2. The finished transdermal therapeutic device had a coating thickness of 100 µm, a weight per unit area of 32 g/square meter and an active component content of 8.9 g/square meter.

3b) Using the acrylate adhesive described in example 1b) and as explained in examples 3a) and 2, an inventive therapeutic system was prepared with a coating thickness of 100 µm, a weight per unit area of 27 g/square meter and an active component content of 7.3 g/square meter.

EXAMPLE 4

In-vitro release tests with transdermal devices produced according to examples 2 and 3

Transdermal therapeutic devices produced in accordance with examples 2 and 3 were tested by the method of T. J. Franz, J. Invest. Dermatol, 1975, vol. 64, pp 191 to 195 on the skin of hairless mice and rats. The results are given in the following table.

| Therapeutic system (example) | Bopindolol hydrogen malonate | Penetrated µg/cm$^2$ | | |
|---|---|---|---|---|
| | | 8 h | 24 h | 0–24 h |
| 2 | 0.84 | 10 | 10 | 20 |
| 3a | 0.89 | 30 | 100 | 130[1] |
| 3a | 0.89 | | | 55[2] |
| 3b | 0.73 | | | 67[2] |

[1] Skin of hairless mice
[2] Skin of hairless rats.

We claim:

1. A transdermal device for delivering a medically active component to skin, comprising an impermeable carrier film and a reservoir applied to the carrier film, wherein the reservoir, when applied, pressure sensitives the skin, wherein the reservoir comprises a mixture of (1) a medically active component selected from the group consisting of antirheumatics, analgesics, blood pressure-influencing products, antiallergics, antiphlogistics, beta-receptor blockers, calcium antagonists, antiasthmatics, dermatics, bleeding-aiding agents, geriatrics, sedatives, cardiacs, coronary agents, antimigraine agents, muscle relaxing agents, neural therapeutics, hormones and their inhibitors, antihyperkinetics and cytostatics, and (2) a pressure sensitive adhesive, wherein the medically active component contains one or more basic nitrogen atoms, and wherein the pressure sensitive adhesive is permeated by the medically active component and consists essentially of a polymer obtained by the polymerization of a) between 30 and 70% by weight of at least one alkyl ester of the group consisting of acrylic and methacrylic acid having 4 to 12 C-atoms in the alkyl radical, b) 5 to 85% by weight of at least one amino ester of an acid selected from the group consisting of acrylic acid, methacrylic acid and other olefins which can be polymerized into a polyacrylate with basic groups, c) 0 to 50% by weight of at least one alkyl ester of the group consisting of acrylic acid and methacrylic acid with 1 to 3 C-atoms in the alkyl radical, d) 0 to 30% by weight of other vinyl compounds which can be polymerised and, e) 0 to 5% by weight of divinyl compounds which can be polymerized, in which the sum of all the percentages in the inventive polymer material is always 100.

2. The transdermal device according to claim 1 wherein the pressure sensitive adhesive is characterized in that the alkyl ester of acrylic acid or methacrylic acid with 1 to 3 C-atoms in the alkyl radical is selected from the group consisting of methyl, ethyl, n-propyl, isopropyl acrylic and methacrylic acid esters and the alkyl ester of acrylic or methacrylic acid with 4 to 12 C-atoms in the alkyl radical is selected from the group consisting of n-butyl, isobutyl, t-butyl, pentyl, hexyl, heptyl, octyl, isooctyl, 2-ethylhexyl, nonyl, decyl, isodecyl, dodecyl acrylic and methacrylic acid esters.

3. Transdermal devive according to claim 1, wherein the divinyl compound is selected from the group consisting of divinyl benzene, 1,3-butadiene, divinyl adipate, diallyl adipate and vinyl acrylate.

4. Transdermal device according to claim 1, wherein the vinyl compound which can be polymerized is selected from the group consisting of vinyl acetate, styrene, methyl vinyl ether, ethyl vinyl ether, n-butyl vinyl ether and vinyl pyrrolidone.

5. Transdermal device according to claim 1, wherein the animo ester is selected from the group consisting of t-butyl aminoethyl, dimethyl aminoethyl, dimethyl aminomethyl, t-butyl aminomethyl, diethyl aminoethyl, diethyl aminomethyl, methylethyl aminoethyl, methylethyl aminomethyl acrylate and methacrylate and substituted aminostryenes and combinations thereof.

6. Transdermal device according to claim 1, wherein the pressure sensitive adhesive is an acrylate-based polymer.

7. Transdermal device according to claim 1, wherein the amount of component c) is 5–20% by weight.

8. Transdermal device according to claim 1, wherein the amount of component d) is 2–15% by weight.

9. Tranedermal device according to claim 1, wherein the amount of component e) is 0.3% by weight.

10. A transdermal device for delivering a medically active component to skin, comprising an impermeable carrier film and a reservoir applied to the carrier film, wherein the reservoir, when applied, pressure sensitives the skin, wherein the reservoir comprises a mixture of (1) a medically active component selected from the group consisting of antirheumatics, analgesics, blood pressure-influencing products, antiallergics, antiphlogistics, beta-receptor blockers, calcium antagonists, antiasthmatics, dermatics, bleeding-aiding agents, geriatrics, sedatives, cardiacs, coronary agents, antimigraine agents, muscle relaxing agents, neural therapeutics, hormones and their inhibitors, antihyperkinetics and cytostatics, and (2) a pressure sensitive adhesive, wherein the medically active component contains one or more basic nitrogen atoms, and wherein the pressure sensitive adhesive is permeated by the medically active component and consists essentially of a polymer obtained by the polymerization of a) between 40 and 60% by weight of at least one alkyl ester of the group consisting of acrylic and methacrylic acid having 4 to 12 C-atoms in the alkyl radical, b) 15 to 50% by weight of at least one amino ester of an acid selected from the group consisting of acrylic acid, methacrylic acid and other olefins which can be polymerized into a polyacrylate with basic groups, c) 5 to 20% by weight of at least one alkyl ester of the group consisting of acrylic acid and methacrylic acid with 1 to 3 C-atoms in the alkyl radical, d) 2 to 15% by weight of other vinyl compounds which can be polymerised and, e) 0.3 to 0.5% by weight of divinyl compounds which can be polymerized, in which the sum of all the percentages in the inventive polymer material is always 100.

11. A transdermal device for delivering a medically active component to skin, comprising an impermeable carrier film and a reservoir applied to the carrier film, wherein the reservoir, when applied, pressure sensitives the skin, wherein the reservoir comprises (1) a pressure sensitive adhesive layer, and (2) a medically active component selected from the group consisting of antirheumatics, analgesics, blood pressure-influencing products, antiallergics, antiphlogistics, beta-receptor blockers, calcium antagonists, antiasthmatics, dermatics, bleeding-aiding agents, geriatrics, sedatives, cardiacs, coronary agents, antimigraine agents, muscle relaxing agents, neural therapeutics, hormones and their inhibitors, antihyperkinetics and cytostatics, wherein the medically active component is interposed between the carrier film and the pressure sensitive adhesive layer, wherein the medically active component contains one or more basic nitrogen atoms, and wherein the pressure sensitive adhesive is permeated by the medically active component and consists essentially of a polymer obtained by the polymerization of a) between 30 and 70% by weight of at least one alkyl ester of the group consisting of acrylic and methacrylic acid having 4 to 12 C-atoms in the alkyl radical, b) 5 to 85% by weight of at least one amino ester of an acid selected from the group consisting of acrylic acid, methacrylic acid and other olefins which can be polymerized into a polyacrylate with basic groups, c) 0 to 50% by weight of at least one alkyl ester of the group consisting of acrylic acid and methacrylic acid with 1 to 3 C-atoms in the alkyl radical, d) 0 to 30% by weight of other vinyl compounds which can be polymerised and, e) 0 to 5% by weight of divinyl compounds which can be polymerized, in which the sum of all the percentages in the inventive polymer material is always 100.

12. The device of claim 1, wherein the medically active component is incorporated into the device in the form of a salt and is converted by the pressure-sensitive adhesive into the corresponding free base.

13. The device of claim 1, wherein the medically active component contains adjuvants.

14. The device of claim 1, wherein the device has a peel-off protective film applied to the reservoir.

15. The device of claim 11, wherein the medically active component contains adjuvants.

16. The device of claim 11, wherein the structure has a peel-off protective film applied to the pressure sensitive adhesive.

17. The device of claim 12, wherein the therapeutically active agent is a Lewis base.

18. The device of claim 1, wherein the medically active component is Bopindolol.

* * * * *